United States Patent [19]

Sawanishi et al.

[11] Patent Number: 5,344,828

[45] Date of Patent: Sep. 6, 1994

[54] PIPERAZINEALKANOIC ACID AND A PHARMACEUTICAL COMPOSITION COMPRISING THE SAME

[75] Inventors: Hiroyuki Sawanishi, Kanazawa; Yasuo Ito, Katsuyama; Hideo Kato, Fukui; Eiichi Koshinaka, Katsuyama; Nobuo Ogawa, Katsuyama; Kouji Morikawa, Katsuyama, all of Japan

[73] Assignee: Hokuriku Pharmaceutical Co., Ltd., Katsuyama, Japan

[21] Appl. No.: 663,154

[22] Filed: Mar. 1, 1991

[30] Foreign Application Priority Data

Mar. 5, 1990 [JP] Japan .................................. 2-51897
Mar. 5, 1990 [JP] Japan .................................. 2-51898
Aug. 29, 1990 [JP] Japan .................................. 2-225256

[51] Int. Cl.$^5$ .................. A61K 31/55; C07D 403/04; C07D 413/04; C07D 417/04
[52] U.S. Cl. ................................... 514/211; 514/217; 540/551; 540/587; 540/579
[58] Field of Search ............... 540/547, 579, 587, 551; 514/211, 214, 217

[56] References Cited

U.S. PATENT DOCUMENTS

| | | | |
|---|---|---|---|
| 3,389,139 | 6/1968 | Schmutz et al. | 540/587 |
| 3,546,226 | 12/1970 | Schmutz et al. | 540/551 |
| 3,845,074 | 10/1974 | Malen et al. | 540/551 |
| 3,928,356 | 12/1975 | Umio et al. | 540/578 |

FOREIGN PATENT DOCUMENTS

| | | |
|---|---|---|
| 0421823 | 4/1991 | European Pat. Off. |
| 0505014 | 9/1992 | European Pat. Off. |
| 1801523 | 6/1969 | Fed. Rep. of Germany |
| 8807997 | 10/1988 | PCT Int'l Appl. |

OTHER PUBLICATIONS

Kaspersen et al. Recl: Journal of the Royal Netherlands Chem. Soc., 102(10), pp. 457–460, (1983).
Chemical Abstract, vol. 100, No. 34501n, (1983), Kaspersen.
Chemical Abstract, 11th Collective Index, 1982–1986 Substance Index.
Stedman's Medical Dictionary, 24th Edition, (Publ. by Williams & Wilkins), p. 133, (1982).

(List continued on next page.)

Primary Examiner—Mukund J. Shah
Assistant Examiner—Philip I. Datlow
Attorney, Agent, or Firm—Cushman, Darby & Cushman

[57] ABSTRACT

Novel polycyclic compounds represented by the following formula: $A-(CH_2)_n-COOR^1$, wherein $R^1$ represents a hydrogen atom or a lower alkyl group; n represents an integer of from 0 to 5; and A is a group represented by the following formula:

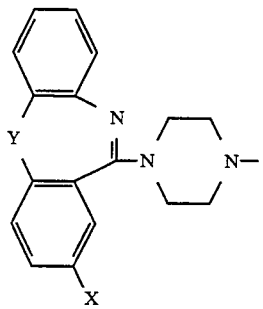

wherein X represents a hydrogen atom or a halogen atom; and Y represents a methylene group, an oxygen atom, or a sulfur atom, or A is a group represented by the following formula:

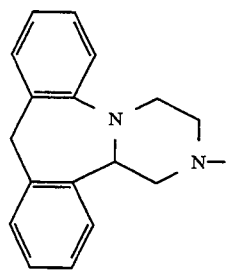

and pharmacologically acceptable salts thereof are disclosed. Also disclosed are a method for preparing the same, a pharmaceutical composition comprising the same, an antiallergic agent and an agent for bronchial asthma comprising the same, and a method for treatment of an allergic disease or bronchial asthma comprising the step of administering the same.

10 Claims, No Drawings

OTHER PUBLICATIONS

Martin et al., "The Pharmacological Properties of a New, Orally Active Antianaphylactic Compound: Ketotifen, a Benzocycloheptathiophene", *Arzneim.-Forsch./Drug Res.*, 28, (1978); (Experiment 2.2.6.), pp. 770–782.

Folia Pharmacol., Japan, 80, (1982), pp. 251–260, Ohmori et al.

"Disodium Cromoglycate (FPL 670) ('Intal'): a Specific Inhibitor of Reaginic Antibody–Antigen Mechanisms", *Nature*, 216, (1967), pp. 1328–1329, Cox.

Howell et al., "A Double-Blind Trial of Disodium Cromoglycate in the Treatment of Allergic Bronchial Asthma", *The Lancet*, 9, (1967), pp. 539–542.

"Ketotifen", Drugs of the Future, 11, (1977), pp. 108–111, Castaner et al.

Partial European Search Report and Annex to the European Search Report on Patent Appln. EP 91-1-0-3059, (1991).

"The Merck Index", Encyclopedia of Chemicals, Drugs, and Biologicals, 11th Ed., (1989), pp. 91, 377, 971, and 1138, Rahway, N.J.

PIPERAZINEALKANOIC ACID AND A PHARMACEUTICAL COMPOSITION COMPRISING THE SAME

BACKGROUND OF THE INVENTION

1. Field of the Invention

The present invention relates to novel polycyclic compounds useful as antihistaminic agents, antiallergic agents, hypo-sedatives, psychoneurotic agents, analgetics, antiemetics, gastrointestinal tract hyperkinetics, antiarrhythmics, and antihypertensive agents.

More specifically, the present invention relates to compounds represented by the following formula (I):

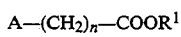   (I)

wherein $R^1$ represents a hydrogen atom or a lower alkyl group; n represents an integer of from 0 to 5; and A is a group represented by the following formula:

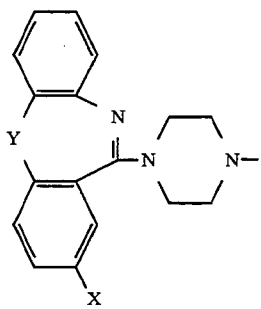

wherein X represents a hydrogen atom or a halogen atom; and Y represents a methylene group, an oxygen atom, or a sulfur atom, or A is a group represented by the following formula:

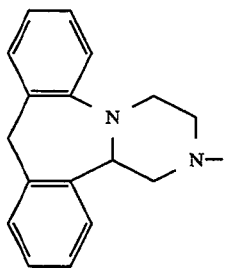

and pharmacologically acceptable salts, which are useful as drugs such as mentioned above.

2. Description of the Related Art

The Merck Index (11th edition) discloses drugs having a polycyclic nucleus similar to that of the compound of the present invention. Examples of such drugs include, for example, Amoxapine represented by the following formula (II):

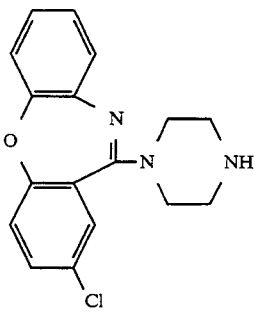

as a antidepressant (11th edition, 609); Clothiapine represented by the following formula (III):

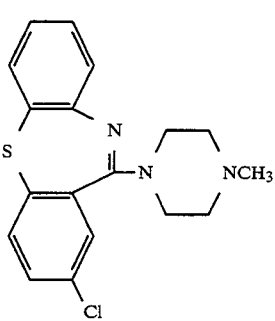

as an antischizophrenic agent (11th edition, 2410): Perlapine represented by the following formula (IV):

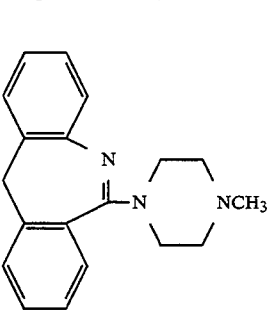

as a hypo-sedative (11th edition, 7131), and Mianserin represented by the following formula (v):

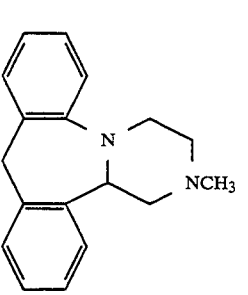

as a antidepressant (11th edition, 6097). However, any documents do not disclose the polycyclic compound of the present invention having a polycyclic nucleus substituted with a carboxyalkyl or alkoxycarbonylalkyl group.

The major defects of these drugs are adverse reactions caused by various kinds of pharmacological actions of the drugs. Examples of the adverse reactions those frequently observed clinically are, for example, psychoneurotic symptoms such as, tremor, hallucinosis, delirium, cerebaria, malaise, vertigo, or anticholinergic symptoms such as hydrodipsia, dysuria, or cycloplegia.

SUMMARY OF THE INVENTION

An object of the present invention is to provide novel compounds having a selective pharmacological activity.

Another object of the present invention is to provide novel compounds which extensively eliminate undesired adverse reactions.

A further object of the present invention is to provide a method for preparing said compounds.

Yet another object is to provide a pharmaceutical composition comprising said compounds.

The inventor of the present invention have conducted various studies to achieve the foregoing objects and found that the objects can be effectively attained by providing novel polycyclic compounds of the present invention. These polycyclic compounds have selective pharmacological activity and reduced adverse reactions and are useful as antihistaminic agents, antiallergic agents, hypo-sedatives, psychoneurotic agents, analgetics, antiemetics, gastrointestinal tract hyperkinetics, antiarrhythmics, or antihypertensive agents.

In accordance with the above objects, the present invention provides a compound represented by the following formula (I):

A—(CH$_2$)$_n$—COOR$^1$       (I)

wherein R$^1$ represents a hydrogen atom or a lower alkyl group; n represents an integer of from 0 to 5; and A is a group represented by the following formula:

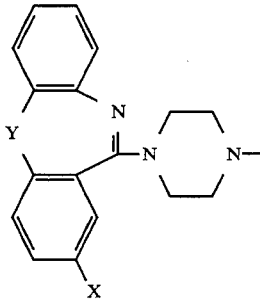

wherein X represents a hydrogen atom or a halogen atom; and Y represents a methylene group, an oxygen atom, or a sulfur atom, or A is a group represented by the following formula:

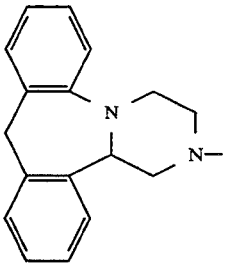

or a pharmacologically acceptable salt of the compound.

In accordance with another embodiment of the present invention, the present invention provides a method for preparing the compound represented by formula (I).

In accordance with yet another embodiment of the present invention, the present invention provides a pharmaceutical composition comprising an effective amount of the compound represented by formula (I) together with a pharmaceutically acceptable carrier or coating.

In accordance with a further embodiment, the present invention provides a method for treating an allergic disease or bronchial asthma comprising the step of administering an effective amount of the compound represented by formula (I) to an mammal.

The present invention also provides an antiallergic agent, antihistaminic agent, and an agent for bronchial asthma comprising the compound represented by formula (I).

Further objects, features and advantages of the present invention will become apparent from the Description of the Preferred Embodiment which follows, when read in light of the attached Examples and Reference Examples.

DESCRIPTION OF THE PREFERRED EMBODIMENT

In the above formula (I), the lower alkyl group represented by R$^1$ may be, for example, methyl, ethyl, n-propyl, isopropyl, n-butyl or isobutyl group, and the halogen atom represented by X may be, for example, a fluorine atom, a chlorine atom, a bromine atom, a iodine atom.

Preferred examples of the present invention include:

ethyl 4-(2-chlorodibenz[b,f][1,4]oxazepin-11-yl)-1-piperazinecarboxylate;

ethyl 4-(2-chlorodibenz[b,f][1,4]oxazepin-11-yl)-1-piperazinepropionate;

ethyl 4-(2-chlorodibenz[b,f][1,4]oxazepin-11-yl)-1-piperazineacetate;

ethyl 4-(2-chlorodibenz[b,f][1,4]oxazepin-11-yl)-1-piperazinebutyrate;

ethyl 4-(2-chlorodibenz[b,f][1,4]oxazepin-11-yl)-1-piperazinevalerate;

ethyl 4-(2-chlorodibenz[b,f][1,4]oxazepin-11-yl)-1-piperazinecaproate;

4-(2-chlorodibenz[b,f][1,4]oxazepin-11-yl)-1-piperazineacetic acid;

4-(2-chlorodibenz[b,f][1,4]oxazepin-11-yl)-1-piperazinepropionic acid;

4-(2-chlorodibenz[b,f][1,4]oxazepin-11-yl)-1-piperazinebutyric acid;

4-(2-chlorodibenz[b,f][1,4]oxazepin-11-yl)-1-piperazinevaleric acid;

4-(2-chlorodibenz[b,f][1,4]oxazepin-11-yl)-1-piperazinecaproic acid;

ethyl 4-(2-chlorodibenzo[b,f][1,4]thiazepin-11-yl)-1-piperazinecarboxylate;

ethyl 4-(2-chlorodibenzo[b,f][1,4]thiazepin-11-yl)-1-piperazinepropionate;

ethyl 4-(2-chlorodibenzo[b,f][1,4]thiazepin-11-yl)-1-piperazineacetate;

ethyl 4-(2-chlorodibenzo[b,f][1,4]thiazepin-11-yl)-1-piperazinebutyrate;

ethyl 4-(2-chlorodibenzo[b,f][1,4]thiazepin-11-yl)-1-piperazinevalerate;

ethyl 4-(2-chlorodibenzo[b,f][1,4]thiazepin-11-yl)-1-piperazinecaproate;

4-(2-chlorodibenzo[b,f][1,4]thiazepin-11-yl)-1-piperazineacetic acid;
4-(2-chlorodibenzo[b,f][1,4]thiazepin-11-yl)-1-piperazinepropionic acid;
4-(2-chlorodibenzo[b,f][1,4]thiazepin-11-yl)-1-piperazinebutyric acid;
4-(2-chlorodibenzo[b,f][1,4]thiazepin-11-yl)-1-piperazinevaleric acid;
4-(2-chlorodibenzo[b,f][1,4]thiazepin-11-yl)-1-piperazinecaproic acid;
ethyl 4-(11H-dibenz[b,e]azepin-6-yl)-1-piperazinecarboxylate;
ethyl 4-(11H-dibenz[b,e]azepin-6-yl)-1-piperazinepropionate;
ethyl 4-(11H-dibenz[b,e]azepin-6-yl)-1-piperazineacetate;
ethyl 4-(11H-dibenz[b,e]azepin-6-yl)-1-piperazinebutyrate;
ethyl 4-(11H-dibenz[b,e]azepin-6-yl)-1-piperazinevalerate;
ethyl 4-(11H-dibenz[b,e]azepin-6-yl)-1-piperazinecaproate;
4-(11H-dibenz[b,e]azepin-6-yl)-1-piperazineacetic acid;
4-(11H-dibenz[b,e]azepin-6-yl)-1-piperazinepropionic acid;
4-(11H-dibenz[b,e]azepin-6-yl)-1-piperazinebutyric acid;
4-(11H-dibenz[b,e]azepin-6-yl)-1-piperazinevaleric acid;
4-(11H-dibenz[b,e]azepin-6-yl)-1-piperazinecaproic acid;
ethyl (1,2,3,4,10,14b-hexahydrodibenzo[c,f]pyrazino[1,2-a]azepin-2-yl)formate;
ethyl 3-(1,2,3,4,10,14b-hexahydrodibenzo[c,f]pyrazino[1,2-a]azepin-2-yl)propionate;
ethyl 2-(1,2,3,4,10,14b-hexahydrodibenzo[c,f]pyrazino[1,2-a]azepin-2-yl)acetate;
ethyl 4-(1,2,3,4,10,14b-hexahydrodibenzo[c,f]pyrazino[1,2-a]azepin-2-yl)butyrate;
ethyl 5-(1,2,3,4,10,14b-hexahydrodibenzo[c,f]pyrazino[1,2-a]azepin-2-yl)valerate;
ethyl 6-(1,2,3,4,10,14b-hexahydrodibenzo[c,f]pyrazino[1,2-a]azepin-2-yl)caproate;
2-(1,2,3,4,10,14b-hexahydrodibenzo[c,f]pyrazino[1,2-a]azepin-2-yl)acetic acid;
3-(1,2,3,4,10,14b-hexahydrodibenzo[c,f]pyrazino[1,2-a]azepin-2-yl)propionic acid;
4-(1,2,3,4,10,14b-hexahydrodibenzo[c,f]pyrazino[1,2-a]azepin-2-yl)butyric acid;
5-(1,2,3,4,10,14b-hexahydrodibenzo[c,f]pyrazino[1,2-a]azepin-2-yl)valeric acid; and
6-(1,2,3,4,10,14b-hexahydrodibenzo[c,f]pyrazino[1,2-a]azepin-2-yl)caproic acid.

The compounds of the present invention represented by the above formula (I) may be converted to pharmacologically acceptable salts, if desired, and may then reconverted to produce the free compound from the obtained salts.

The pharmacologically acceptable salts of the compounds the present invention represented by formula (I) may be acid addition salts or alkali addition salts. Examples of the acid addition salts include mineral acid addition salts such as, for example, hydrochloride, hydrobromide, sulfate, nitrate, phosphate, and organic acid addition salts such as, for example, acetate, maleate, fumarate, malate, citrate, oxalate, lactate, and tartarate. Examples of the alkali addition salts include metal salts such as, for example, sodium, potassium, carcium salt, and organic alkali salts such as, for example, ammonium salts, methylamine, ethylamine, dimethylamine, triethylamine, ethanolamine, piperidine, and piperazine salts.

According to an embodiment of the present invention, the novel polycyclic compounds of the present invention represented by formula (I) can be prepared by the method comprising the steps reacting a compound represented by the following formula (VI):

A—H (VI)

wherein A is the same as that defined above, with a compound represented by the following formula (VII):

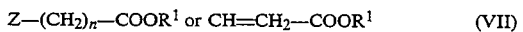

Z—(CH$_2$)$_n$—COOR$^1$ or CH=CH$_2$—COOR$^1$ (VII)

wherein R$^1$ and n are the same as those defined above, and Z represents a halogen atom, in a solvent or without solvent in the presence or absence of a base as a dehydrohalogenating agent, and followed by hydrolysis in a solvent by using an acid or a base, if necessary.

Any inert solvent may be used in the alkylation process of the present invention. Examples of the inert solvent include benzene, toluene, tetrahydrofuran, dioxane, acetone, acetonitrile, methanol, ethanol, isopropanol, n-butanol, dimethyl sulfoxide, and N,N-dimethylformamide.

Examples of the base used in the process of the present invention include potassium carbonate, sodium carbonate, pyridine, and triethylamine. The reaction may be carried out at from 0° to 200° C.

For the hydrolysis process, an acid such as, for example, hydrochloric acid or sulfuric acid, or a base such as, for example, sodium hydroxide, potassium hydroxide, potassium carbonate, sodium carbonate, or sodium bicarbonate may be used. A solvent used in the hydrolysis may be, for example, water, methanol, ethanol, acetone, or tetrahydrofuran, and the hydrolysis may be carried out at from 0° to 100° C.

In addition, the compounds represented by the above formula (VI), used as starting materials for the above process, are disclosed in Helvetica Chimica Acta, 50, 245–254; British Patent No. 1,006,156; and U.S. Pat. No. 4,217,452.

According to another embodiment of the present invention, the novel polycyclic compounds of the present invention represented by formula (I) wherein n is 0, can be prepared by the method comprising the steps of reacting a compound represented by the following formula (VIII):

A—CH$_3$ (VIII)

wherein A is the same as that defined above, with a compound represented by the following formula (IX):

Z—COOR$^1$ (IX)

wherein R$^1$ and Z are the same as those defined above, in a solvent in the presence or absence of a base as dehydrohalogenating agent.

Any inert solvent may be used in the alkylation process of the present invention. Examples of the inert solvent include benzene, toluene, tetrahydrofuran, dioxane, acetone, acetonitrile, methanol, ethanol, isopropanol, n-butanol, dimethyl sulfoxide, and N,N-dimethylformamide.

Examples of the base used in the process of the present invention include potassium carbonate, sodium carbonate, pyridine, and triethylamine. The reaction may be carried out at from 0° to 200° C.

The novel polycyclic compounds of the present invention represented by the above formula (I) and pharmacologically acceptable salts of the compounds are useful as antihistaminic agents., antiallergic agents, hypo-sedatives, psychoneurotic agents, analgetics, antiemetics, gastrointestinal tract hyperkinetics, antiarrhythmics, or antihypertensive agents.

The novel polycyclic compounds of the present invention and their pharmacologically acceptable salts may be administered orally or parenterally to a patient as a pharmaceutical composition which comprises an effective amount of said compound or the salt thereof together with a pharmacologically acceptable carrier or coating.

The pharmaceutical composition suitable for oral administration may be, for example, tablet, capsule, powder, subtilized granule, granule, solution, or syrup. The pharmaceutical composition suitable for parenteral administration may be injection, suppository, inhalant, eye drop, nasal drop, ointment, or cataplasm. The pharmaceutically acceptable carrier or coating used for the preparation of the pharmaceutical composition may be excipient, disintegrant or agent for accelerating disintegration, binder, lubricant, coating agent, pigment, diluent, base, solubilizing agent, solubilizer, isotonicity, pH adjusting agent, stabilizer, propellant, and adhesive.

For the preparation of the pharmaceutical composition suitable for oral administration, dermal administration, or mucosal application, the coating or carrier may comprise the following: an excipient such as, for example, glucose, lactose, D-mannitol, starch, or crystalline cellulose; a disintegrant or an agent for accelerating disintegration such as, for example, carboxymethylcellulose, starch, or calcium carboxymethylcellulose; a binder such as, for example, hydroxypropylcellulose, hydroxypropylmethylcellulose, polyvinylpyrrolidone, or gelatin; a lubricant such as, for example, magnesium stearate or talc; a coating agent such as, for example, hydroxypropylmethylcellulose, sucrose, polyethylene glycol, or titanium oxide; a base such as, for example, petrolatum, liquid paraffin, polyethyleneglycol, gelatin, kaolin, glycerin, purified water, or hard fat; a propellant such as, for example, fron, diethyl ether, compressed gas; an adhesive such as, for example, sodium polyacrylate, polyvinylalcohol, methylcellulose, polyisobutylene, or polybutene; or a base sheet such as, for example, cloth or plastic sheet. The pharmaceutical composition suitable for injection may comprise the following: a solubilizing agent or a solubilizer, e.g., distilled water for injection, saline, or propylene glycol which is useful for an aqueous composition or a composition for preparing aqueous solution before use; an isotonicity agent such as, for example, glucose, sodium chloride, D-mannitol, or glycerin; and a pH adjusting agent such as, for example, an inorganic or organic acid or an inorganic or organic base.

The dose of the pharmaceutical composition of the present invention for an adult patient may generally be from about 1 to 500 mg per day for oral administration, which may be increased or decreased depending on the conditions of the patient to be treated.

The present invention will be further illustrated by the following Examples. The Examples are given by way of illustration only and are not to be construed as limiting.

EXAMPLES

The following examples show the excellent effectiveness of the compounds of the present invention. The results of antihistaminic and antiallergic activities are summarized in Tables 1 and 2, respectively.

The reference compounds used were Amoxapine (II), Clothiapine (III), Perlapine (IV) and Mianserin (V).

1. Antihistaminic activity (Effect on the contractile response induced by histamine in isolated guinea-pig ileum)

Male Hartley guinea-pigs, 5–8 weeks of age, were sacrificed and the ileum was excised. An approximately 20 mm strip of isolated ileum was mounted vertically under a 0.5 g load in an organ bath containing 10 ml of Locke-Ringer solution (NaCl: 154 mM, KCl: 5.6 mM, $CaCl_2.2H_2O$: 2.2 mM, $MgCl_2.6H_2O$: 2.1 mM, $NaHCO_3$: 5.9 mM, glucose: 2.8 mM ) maintained at 28° C. and bubbled with 95% $O_3$ and 5% $CO_2$. The contractile response was recorded on a recticorder an isotonic transducer. The concentration-contractile response curve to histamine was constructed before and after 30 min contact with test compounds. The dissociation constant $K_B$ (M) of test compounds was calculated according to the method of Furchgott ("Catecholamines" Edited by Blaschko, H. and Muscholl, E., 283–335, Springer, Berlin; Heidelberg and New York, 1972).

The results are shown in Table 1.

TABLE 1

| | Antihistaminic Activity | | |
|---|---|---|---|
| Test compound | $-\log K_B$ | Test compound | $-\log K_B$ |
| Example 2 | 7.92 | Example 28 | 7.76 |
| Example 4 | 8.31 | Example 30 | 7.24 |
| Example 5 | 7.98 | Example 32 | 7.24 |
| Example 6 | 8.51 | Example 33 | 7.57 |
| Example 8 | 7.30 | Example 35 | 8.57 |
| Example 9 | 7.32 | Example 36 | 7.49 |
| Example 10 | 7.26 | Example 37 | 8.62 |
| Example 13 | 7.29 | Example 38 | 7.96 |
| Example 15 | 7.52 | Example 39 | 7.89 |
| Example 16 | 7.33 | Example 40 | 7.74 |
| Example 17 | 7.26 | Example 41 | 7.60 |
| Example 19 | 7.28 | Example 42 | 7.51 |
| Example 20 | 7.24 | Example 43 | 7.32 |
| Example 21 | 7.23 | Example 44 | 7.49 |
| Example 22 | 7.46 | | |
| Example 24 | 8.05 | Amoxapine | 8.37 |
| Example 25 | 7.34 | Clothiapine | 8.87 |
| Example 26 | 7.87 | Perlapine | 9.15 |
| Example 27 | 8.10 | Mianserin | 9.15 |

The compounds of the present invention exhibited excellent activities, though the activities were somewhat less potent than those of the reference compounds.

2. Antiallergic activity (48 hr homologous passive cutaneous anaphylaxis (PCA) in rat)

Male Wistar rats, 6 weeks of age, were passively sensitized by intracutaneous injection in the back of a volume of 0.1 ml of anti-DNP-As rat serum. Forty-eight hours later, the animals were administered an intravenous injection of 0.5 ml saline solution containing 1 mg of DNP-As and 5 mg of Evans blue. The animals were sacrificed 30 min after the injection and the extravasated dye was extracted with 1N KOH and acetone, neutralized with 1N $H_3PO_4$ and the absorbance at 620 nm was determined. The test compounds were administered orally in a dose of 1 mg/Kg 1 hr before antigen challenge. The inhibitory activity of a test compound was expressed as percent inhibition of PCA as compared with the control group. The results are shown in Table 2.

TABLE 2

| Antiallergic Activity | | | |
|---|---|---|---|
| Test compound | Inhibition rate (%) | Test compound | Inhibition rate (%) |
| Example 8 | 88.6 | Example 41 | 76.5 |
| Example 9 | 95.8 | Example 42 | 65.6 |
| Example 10 | 84.1 | Example 43 | 73.9 |
| Example 11 | 86.4 | Example 44 | 71.8 |
| Example 19 | 64.6 | | |
| Example 20 | 77.7 | Amoxapine | 50.9 |
| Example 21 | 78.5 | Mianserin | 61.4 |
| Example 22 | 77.2 | | |

The compounds of the present invention exhibited more potent antiallergic activity than the reference compounds.

The inhibitory activity of noradrenaline and 5hydroxytryptamine uptake and anticholinergic activity were also examined. The compounds of the present invention showed little activity, while the reference compounds showed considerable activity.

Since the compounds of the present invention hardly have the above activity, these compounds, and because they cause no side effects such as, for example, psychogenesis, dipsia and dysuria derived from these activities, are expected to be excellent, selective antihistaminic and antiallergic agents.

Example 1

Ethyl 4-(2-Chlorodibenz[b,f][1,4]oxazepin-11-yl)-1-piperazinecarboxylate

A mixture of 2.20 g of 2-chloro-11-(1-piperazinyl)-dibenz[b,f][1,4]oxazepine, 0.76 g of ethyl chloroformate and 0.97 g of potassium carbonate in 20 ml of N,N-dimethylformamide was stirred at 80° C. for 3 hrs. Ice water was added to the reaction mixture and extracted with ether. The etheral layer was washed with water, dried and concentrated. The residue was chromatographed on silica gel using a mixture of n-hexane and ethyl acetate (1:2) as eluents to give 2.62 g of colorless crystals, which were recrystallized from isopropyl ether to give colorless prisms, mp 121.5°-122.5° C.

Analysis for $C_{20}H_{20}ClN_3O_3$ Calculated C,62.26; H,5.22; N,10.89 Found C,62.36; H,5.04; N,11.00

Example 2

Ethyl 4-(2-Chlorodibenz[b,f][1,4]oxazepin-11-yl)-1-piperazinepropionate

A mixture of 3.14 g of 2-chloro-11-(1-piperazinyl)-dibenz[b,f][1,4]oxazepine and 1.20 g of ethyl acrylate in 16 ml of ethanol was refluxed for 2 hrs. The reaction mixture was concentrated and the residue was chromatographed on silica gel using a mixture of n-hexane and ethyl acetate (2:1 and 1:1) as eluents to give 3.68 g of yellow crystals, which were recrystallized from a mixture of isopropyl ether and n-pentane to give yellow prisms, mp 73°-75° C.

Analysis for $C_{22}H_{24}ClN_3O_3$ Calculated C,63.84; H,5.84; N,10.15 Found C,63.95; H,5.86; N,10.16

Example 3

Ethyl 4-(2-Chlorodibenz[b,f][1,4]oxazepin-11-yl)-1-piperazineacetate

A mixture of 3.4 g of 2-chloro-11-(1-piperazinyl)-dibenz[b,f][1,4]oxazepine, 2.00 g of ethyl bromoacetate and 1.38 g of potassium carbonate in 16 ml of N,N-dimethylformamide was stirred at 60°-70° C. for 3 hrs. After cooling, water was added to the reaction mixture and extracted with ether. The etheral layer was washed with water, dried and concentrated. The residue was chromatographed on silica gel using a mixture of n-hexane and ethyl acetate (2:1 and 1:1) as eluents to give 3.12 g of yellow crystals, which were recrystallized from n-hexane to give yellow prisms, mp 123°-123.5° C.

Analysis for $C_{21}H_{22}ClN_3 O_3$ Calculated C,63.07; H,5.55; N,10.51 Found C,63.26; H,5.56; N,10.60

The compounds of Example 4 to 6 were prepared in the same manner as described in Example 3.

Example 4

Ethyl 4-(2-Chlorodibenz[b,f][1,4]oxazepin-11-yl)-1-piperazinebutyrate

Yellow prisms, mp 86°-87° C. (n-hexane)

Analysis for $C_{23}H_{26}ClN_3O_3$ Calculated C,64.56; H,6.12; N,9.82 Found C,64.58; H,6.20; N,9.82

Example 5

Ethyl 4-(2-Chlorodibenz[b,f][1,4]oxazepin-11-yl)-1-piperazinevalerate

Yellow prisms, mp 82.5°-84° C. (iso-Pr$_2$O-n-pentane)

Analysis for $C_{24}H_{28}ClN_3O_3$ Calculated C,65.22; H,6.39; N,9.51 Found C,65.18; H,6.48; N,9.36

Example 6

Ethyl 4-(2-Chlorodibenz[b,f][1,49 oxazepin-11-yl)-1-piperazinecaproate

Pale yellowish viscous oil

IR spectrum ν (liq) cm$^{-1}$: 1738 (COO) NMR spectrum δ(CDCl$_3$) ppm: 1.10-2.80(14H,m),1.28(3H,t,J=7.0 Hz), 3.40-3.75(4H,m),4.19(2H,q,J=7.0 Hz), 7.00-7.65(7H,m)

High resolution mass spectrum for $C_{25}H_{30}ClN_3O_3$ Calculated m/z: 455.1976 Found m/z: 455.1994

Example 7

4-(2-Chlorodibenz[b,f][1,4]oxazepin-11-yl)-1-piperazineacetic acid

2N Aqueous sodium hydroxide solution (5 ml) was added to a solution of 2.00 g of ethyl 4-(2-chlorodibenz[b,f][1,4]oxazepin-11-yl)-1-piperazineacetate in 20 ml of methanol. The solution was refluxed for 30 min and then concentrated. The residue was dissolved in hot water and the solution was neutralized with 0.5N hydrochloric acid. The precipitates were collected by filtration to give 1.67 g of colorless crystals, which were recrystallized from aqueous ethanol to give colorless crystals, mp 210°-212° C.

IR spectrum ν (KBr) cm$^{-1}$: 1608 (COO$^-$) Mass spectrum m/z: 371,373 (M$^+$,3:1) NMR spectrum δ(DMSO-d$_6$) ppm: 2.50-2.90(4H,m),3.24(2H,s),3.-30-3.70(4H,m),7.00-7.80(7H,m)

The compounds of Example 8 to 11 were prepared in the same manner as described in Example 7.

Example 8

4-(2-Chlorodibenz[b,f][1,4]oxazepin-11-yl)-1-piperazinepropionic acid

Colorless crystals, mp 122°–124° C. (H$_2$O-EtOH).

IR spectrum ν (KBr) cm$^{-1}$: 1604 (COO$^-$) Mass spectrum m/z: 385,387 (M$^+$,3:1) NMR spectrum δ(DMSO-d$_6$) ppm: 2.30–2.80(8H,m),3.30–3.70(4H,m),6.90–7.80(7H,m)

Example 9

4-(2-Chlorodibenz[b,f][1,4]oxazepin-11-yl)-1-piperazinebutyric acid

Pale yellow crystals, mp 120°–122° C. (H$_2$O-EtOH).

IR spectrum ν (KBr) cm$^{-1}$: 1604 (COO$^-$) Mass spectrum m/z: 399,401 (M$^+$,3:1) NMR spectrum δ(DMSO-d$_6$) ppm: 1.50–2.00(2H,m),2.10–2.70(8H,m),3.30–3.70(4H,m),7.00–7.80(7H,m)

Example 10

4-(2-Chlorodibenz[b,f][1,4]oxazepin-11-yl)-1-piperazinevaleric acid

Colorless crystals, mp 223°–226° C. (H$_2$O-EtOH)

Analysis for C$_{22}$H$_{24}$ClN$_3$O$_3$ Calculated C,63.84; H,5.84; N,10.15 Found C,63.72; H,5.89; N,10.07

Example 11

4-(2-Chlorodibenz[b,f][1,49 oxazepin-11-yl)-1-piperazinecaproic acid

Pale yellow crystals, mp 173°–175° C. (H$_2$O-EtOH)

Analysis for C$_{23}$H$_{26}$ClN$_3$O$_3$ Calculated C,64.56; H,6.12; N,9.82 Found C,64.54; H,6.11; N,9.83

Example 12

Ethyl 4-(2-Chlorodibenzo [b,f][1,4]thiazepin-11-yl)-1-piperazinecarboxylate

A mixture of 0.86 g of 2-chloro-11-(4-methyl-1-piperazinyl)dibenzo[b,f][1,4]thiazepine and 0.81 g of ethyl chloroformate in 5 ml of toluene was refluxed for 5 hrs. Ice water was added to the reaction mixture and made alkaline with sodium bicarbonate. The mixture was extracted with methylene chloride and the methylene chloride layer was washed with water, dried and concentrated. The residue was chromatographed on silica gel using methylene chloride as an eluent to give 0.70 g of colorless crystals, which were recrystallized from a mixture of isopropyl ether and n-pentane to give colorless prisms, mp 96.5°–97.5° C.

Analysis for C$_{20}$H$_{20}$ClN$_3$O$_2$S Calculated C,59.77; H,5.02; N,10.46 Found C,60.00; H,5.06; N,10.39

Example 13

Ethyl 4-(2-Chlorodibenzo[b,f][1,4]thiazepin-11-yl)-1-piperazinepropionate

A mixture of 3.30 g of 2-chloro-11-(1-piperazinyl)-dibenzo[b,f][1,4]thiazepine and 1.20 g of ethyl acrylate in 17 ml of ethanol was refluxed for 3 hrs. The reaction mixture was concentrated and the residue was chromatographed on silica gel using a mixture of n-hexane and ethyl acetate (1:1) as an eluent to give 4.04 g of yellow crystals, which were recrystallized from isopropyl ether to give colorless needles, mp 79°–80° C.

Analysis for C$_{22}$H$_{24}$ClN$_3$O$_2$S Calculated C,61.47; H,5.63; N,9.77 Found C,61.28; H,5.81; N,9.64

Example 14

Ethyl 4-(2-Chlorodibenzo[b,f][1,4]thiazepin-11-yl)-1-piperazineacetate

A mixture of 3.30 g of 2-chloro-11-(1-piperazinyl)-dibenzo[b,f][1,4]thiazepine, 2.00 g of ethyl bromoacetate and 1.38 g of potassium carbonate in 17 ml of N,N-dimethylformamide was stirred at 70° C. for 3 hrs. After cooling, water was added to the reaction mixture and extracted with ether. The etheral layer was washed with water, dried and concentrated. The residue was chromatographed on silica gel using a mixture of n-hexane and ethyl acetate (1:1) as an eluent to give 3.95 g of pale yellow crystals.

IR spectrum ν (KBr) cm$^{-1}$: 1744 (COO) NMR spectrum δ(CDCl$_3$) ppm: 1.27(3H,t,J=7 Hz),2.50–3.00(4H,m), 3.27(2H,s),3.40–3.85(4H,m), 4.20(2H,q,J=7 Hz),6.70–7.60(7H,m)

High resolution mass spectrum for C$_{21}$H$_{22}$ClN$_3$O$_2$S Calculated m/z: 415.1121, 417.1092 Found m/z: 415.1097, 417.1087

The compounds of Example 15 to 17 were prepared in the same manner as described in Example 14.

Example 15

Ethyl 4-(2-Chlorodibenzo [b,f ][1,4]thiazepin-11-yl)-1-piperazinebutyrate

Yellowish viscous oil

IR spectrum ν (liq) cm$^{-1}$: 1736 (COO) NMR spectrum δ(CDCl$_3$) ppm: 1.30(3H,t,J=7 Hz),1.65–2.20(2H,m),2.25–2.80(8H,m),3.30–3.80(4H,m), 4.18(2H,q,J=7 Hz),6.70–7.60(7H,m)

High resolution mass spectrum for C$_{23}$H$_{26}$ClN$_3$O$_2$S Calculated m/z: 443.1434, 445.1405 Found m/z: 443.1441, 445.1418

Example 16

Ethyl 4-(2-Chlorodibenzo[b,f][1,4]thiazepin-11-yl)-1-piperazinevalerate

Yellowish viscous oil

IR spectrum ν (liq) cm$^{-1}$: 1738 (COO) NMR spectrum δ(CDCl$_3$) ppm: 1.25(3H,t,J=7 Hz),1.59–1.90(4H,m),2.5–2.70(8H,m),3.35–3.70(4H,m), 4.15(2H,q,J=7 Hz),6.70–7.60(7H,m)

High resolution mass spectrum for C$_{24}$H$_{28}$ClN$_3$O$_2$S Calculated m/z: 457.1591, 459.1561 Found m/z: 457.1518, 459.1553

Example 17

Ethyl 4-(2-Chlorodibenzo[b,f][1,4]thiazepin-11-yl)-1piperazinecaproate

Yellowish viscous oil

IR spectrum ν (liq) cm$^{-1}$: 1740 (COO) NMR spectrum δ(CDCl$_3$) ppm: 1.25(3H,t,J=7 Hz),1.30–2.00(6H,m),2.00–2.80(8H,m),3.40–3.80(4H,m), 4.15(2H,q,J=7 Hz),6.70–7.60(7H,m)

High resolution mass spectrum for C$_{25}$H$_{30}$ClN$_3$O$_2$S Calculated m/z: 471.1747, 473.1718 Found m/z: 471.1753, 473.1746

Example 18

4-(2-Chlorodibenzo[b,f ][1,4]thiazepin-11-yl)-1-piperazineacetic acid

2N Aqueous sodium hydroxide solution (5 ml) was added to a solution of 2.08 g of ethyl 4-(2-chlorodibenzo[b,f][1,4]thiazepin-11-yl)-1-piperazineacetate in 21 ml of methanol. The solution was refluxed for 30 min and then concentrated. The residue was dissolved in hot water and the solution was neutralized with 0.5N hydrochloric acid. The yellowish viscous precipitates were extracted with chloroform. The chloroform layer was washed with water, dried and concentrated to give 1.89 g of pale yellow crystals, which were recrystallized from ethanol to give pale yellow crystals, mp 139°–141° C.

Analysis for C$_{19}$H$_{18}$ClN$_3$O$_2$S.H$_2$O Calculated C,56.22; H,4.97; N,10.35 Found C,56.41; H,4.71; N,10.55

Example 19

4-(2-Chlorodibenzo[b,f][1,4]thiazepin-11-yl)-1-piperazinepropionic acid

2N Aqueous sodium hydroxide solution (5 ml) was added to a solution of 2.15 g of ethyl 4-(2-chlorodibenzo[b,f][1,4]thiazepin-11-yl)-1-piperazinepropionate in 22 ml of methanol. The solution was refluxed for 30 min and then concentrated. The residue was dissolved in hot water and the solution was neutralized with 0.5N hydrochloric acid. The precipitates were collected by filtration to give 1.84 g of pale yellow crystals, which were recrystallized from aqueous ethanol to give pale yellow crystals, mp 120°–121° C.

Analysis for $C_{20}H_{20}ClN_3O_2S.2H_2O$ Calculated C,54.85; H,5.52; N,9.59 Found C,54.76; H,5.44; N,9.46

The compounds of Example 20 to 22 were prepared in the same manner as described in Example 19.

Example 20

4-(2-Chlorodibenzo[b,f][1,4]thiazepin-11-yl)-1-piperazinebutyric acid

Colorless crystals, mp 112°–114° C. ( $H_2O$-EtOH )

Analysis for $C_{21}H_{22}ClN_3O_2S.H_2O$ Calculated C,58.12; H,5.57; N,9.68 Found C,57.95; H,5.38; N,9.75

Example 21

4-(2-Chlorodibenzo [b,f ][1,4]thiazepin-11-yl)-1-piperazinevaleric acid

Colorless prisms, mp 220–221° C. ($H_2O$-EtOH)

Analysis for $C_{22}H_{24}ClN_3O_2S$ Calculated C,61.46; H,5.63; N,9.77 Found C,61.40; H,5.55; N,9.72

Example 22

4-(2-Chlorodibenzo[b,f][1,4]thiazepin-11-yl)-1-piperazinecaproic acid

Pale yellow prisms, mp 186°–187° C. ($H_2$-EtOH)

Analysis for $C_{23}H_{26}ClN_3O_2S$ Calculated C,62.22; H,5.90; N,9.46 Found C,62.02; H,5.87; N,9.32

Example 23

Ethyl 4-(11H-Dibenz[b,e]azepin-6-yl)-1-piperazinecarboxylate

A mixture of 3.33 g of 6-(1-piperazinyl)-11H-dibenz[b,e]azepine, 1.63 g of ethyl chloroformate and 1.66 g of potassium carbonate in 20 ml of N,N-dimethylformamide was stirred at 80° C. for 3 hrs. Ice water was added to the reaction mixture and extracted with ether. The ether layer was washed with water, dried and concentrated. The residue was chromatographed on silica gel using a mixture of n-hexane and ethyl acetate (1:2) as an eluent to give 3.14 g of colorless crystals, which were recrystallized from isopropyl ether to give colorless prisms, mp 137°–138° C.

Analysis for $C_{21}H_{23}N_3O_2$ Calculated C,72.18; H,6.63; N,12.03 Found C,71.94; H,6.68; N,11.96

Example 24

Ethyl 4-(11H-Dibenz[b,e]azepin-6-yl)-1-piperazinepropionate

A mixture of 2.77 g of 6-(1-piperazinyl)-11H-dibenz[b,e]azepine and 1.20 g of ethyl acrylate in 14 ml of ethanol was refluxed for 2 hrs. The reaction mixture was concentrated and the residue was chromatographed on silica gel using a mixture of n-hexane and ethyl acetate (1:1) as an eluent to give 3.25 g of colorless crystals, which were recrystallized from isopropyl ether to give colorless prisms, mp 133°–134° C.

Analysis for $C_{23}H_{27}N_3O_2$ Calculated C,73.18; H,7.21; N,11.13 Found C,73.15; [t,7.26; N,11.10

Example 25

Ethyl 4-(11H-Dibenz[b,e]azepin-6-yl)-1-piperazineacetate

A mixture of 2.77 g of 6-(1-piperazinyl)-11H-dibenz[b,e]azepine, 2.00 g of ethyl bromoacetate and 1.38 g of potassium carbonate in 14 ml of N,N-dimethylformamide was stirred at 70° C. for 3 hrs. After cooling, water was added to the reaction mixture and extracted with ether. The etheral layer was washed with water, dried and concentrated. The residue was chromatographed on silica gel using a mixture of n-hexane and ethyl acetate (2:1 and 1:1) as eluents to give 2.91 g of colorless crystals, which were recrystallized from isopropyl ether to give colorless prisms, mp 107°–108° C.

Analysis for $C_{22}H_{25}N_3O_2$ Calculated C,72.70; H,6.93; N,11.56 Found C,72.76; H,6.78; N,11.53

The compounds of Example 26 to 28 were prepared in the same manner as described in Example 25.

Example 26

Ethyl 4-(11H-Dibenz[b,e]azepin-6-yl)-1-piperazinebutyrate

Pale yellow prisms, mp 106°–107° C. (iso-$Pr_2O$)

Analysis for $C_{24}H_{29}N_3O_2$ Calculated C,73.63; H,7.47; N,10.73 Found C,73.39; H,7.54; N,10.54

Example 27

Ethyl 4-(11H-Dibenz[b,e]azepin-6-yl)-1-piperazinevalerate

Colorless prisms, mp 57°–58° C. (iso-$Pr_2O$-n-pentane)

Analysis for $C_{25}H_{31}N_3O_2$ Calculated C,74.04; H,7.70; N,10.36 Found C,74.22; H,7.81; N,10.40

Example 28

Ethyl 4-(11H-Dibenz[b,e]azepin-6-yl)-1-piperazinecaproate

Colorless prisms, mp 62.5°–63° C. (iso-$Pr_2O$-n-pentane)

Analysis for $C_{26}H_{33}N_3O_2$ Calculated C,74.43; H,7.93; N,10.02 Found C,74.48; H,7.83; N, 9.97

Example 29

4-(11H-Dibenz[b,e]azepin-6-yl)-1-Piperazineacetic acid

2N Aqueous sodium hydroxide solution (5 ml) was added to a solution of 1.82 g of ethyl 4-(11H-dibenz[b,e]azepin-6-yl)-1-piperazineacetate in 18 ml of methanol. The solution was refluxed for 30 min and then concentrated. The residue was dissolved in hot water and the solution was neutralized with 0.5N hydrochloric acid. The precipitates were collected by filtration to give 1.06 g of colorless crystals, which were recrystallized from ethanol to give colorless granules, mp 181°–183° C. (decomp.).

Analysis for $C_{20}H_{21}N_3O_2.H_2O$ Calculated C,67.97; H,6.56; N,11.89 Found C,67.74; H,6.40; N,11.82

The compounds of Example 30 to 33 were prepared in the same manner as described in Example 29.

Example 30

4-(11H-Dibenz[b,e]azepin-6-yl)-1-piperazinepropionic acid

Colorless prisms, mp 140°–141° C. (aq. EtOH)

Analysis for $C_{21}H_{23}N_3O_2.2H_2O$ Calculated C,65.44; H,7.06; N, 10.90 Found C,65.44; H,7.02; N, 10.85

Example 31

4-(11H-Dibenz[b,e]azepin-6-yl)-1-piperazinebutyric acid

Colorless prisms, mp 207°–208° C. (aq. EtOH)

Analysis for $C_{22}H_{25}N_3O_2$ Calculated C,72.70; H,6.93; N,11.56 Found C,72.73; H,7.13; N,11.59

Example 32

4-(11H-Dibenz[b,e]azepin-6-yl)-1-piperazinevaleric acid

Colorless granules, mp 235°–237° C. (aq. EtOH)

Analysis for $C_{23}H_{27}N_3O_2$ Calculated C,73.18; H,7.21; N,11.13 Found C,73.01; H,7.19; N,11.20

Example 33

4-(11H-Dibenz[b,e]azepin-6-yl)-1-piperazinecaproic acid

Colorless prisms, mp 99°–100° C. (aq. EtOH)

Analysis for $C_{24}H_{29}N_3O_2 \cdot H_2O$ Calculated C,70.39; H,7.63; N,10.26 Found C,70.29; H,7.54; N,10.24

Example 34

Ethyl (1,2,3,4,10,14b-Hexahydrodibenzo[c,f]pyrazino[1,2-a]azepin-2-yl)formate

Ethyl chloroformate (19.53 g) was added dropwisely to a solution of 9.52 g of 1,2,3,4,10,14b-hexahydro-2-methyldibenzo[c,f]pyrazino[1,2-a]azepine in 48 ml of benzene at refluxed temperature and the mixture was refluxed for 5 hrs. Ice water was added to the reaction mixture and made alkaline with sodium bicarbonate. The mixture was extracted with benzene and the benzene layer was washed with water, dried and concentrated. The residue was chromatographed on silica gel using a mixture of n-hexane and ethyl acetate as an eluent (1:2) to give 8.70 g of pale yellow crystals, which were recrystallized from a mixture of isopropyl ether and n-pentane to give pale yellow prisms, mp 108.5°–109.5° C.

Analysis for $C_{20}H_{22}N_2O_2$ Calculated C,74.51; H,6.88; N,8.69 Found C,74.43; H,7.06; N,8.57

Example 35

Ethyl 3-(1,2,3,4,10,14b-Hexahydrodibenzo[c,f]pyrazino[1,2-a]azepin-2-yl)propionate A mixture of 2.50 g of 1,2,3,4,10,14b-hexahydrodibenzo[c,f]pyrazino[1,2-a]azepine and 1.20 g of ethyl acrylate in 13 ml of ethanol was refluxed for 3 hrs. The reaction mixture was concentrated and the residue was chromatographed on silica gel using a mixture of n-hexane and ethyl acetate (1:1) as an eluent to give 3.08 g of colorless crystals, which were recrystallized from isopropyl ether to give colorless needles, mp 159°–160° C.

Analysis for $C_{22}H_{26}N_2O_2$ Calculated C,75.40; H,7.48; N,7.99 Found C,75.35; H,7.58; N,7.79

Example 36

Ethyl 2-(1,2,3,4,10,14b-Hexahydrodibenzo[c,f]pyrazino[1,2-a]azepin-2-yl)acetate

A mixture of 2.50 g of 1,2,3,4,10,14b-hexahydrodibenzo[c,f]pyrazino[1,2-a]azepine, 2.00 g of ethyl bromoacetate and 1.38 g of potassium carbonate in 13 ml of N,N-dimethylformamide was stirred at 70° C. for 3 hrs. After cooling, water was added to the reaction mixture and extracted with ether. The etheral layer was washed with water, dried and concentrated. The residue was chromatographed on silica gel using a mixture of n-hexane and ethyl acetate (1:1) as an eluent to give 3.20 g of pale yellow crystals.

IR spectrum $\nu$ (KBr) cm$^{-1}$: 1748 (COO) NMR spectrum $\delta$(CDCl$_3$) ppm: 1.27(3H,t,J=7 Hz),2.30–3.70(7H,m), 3.30(2H,s),4.00–4.40(3H,m), 4.82(1H,d,J=13 Hz),6.65–7.25(8H,m)

High resolution mass spectrum for $C_{21}H_{24}N_2O_2$ Calculated m/z: 336.1837 Found m/z: 336.1803

The compounds of Example 37 to 39 were prepared in the same manner as described in Example 36.

Example 37

Ethyl 4-(1,2,3,4,10,14b-Hexahydrodibenzo[c,f]pyrazino[1,2-a]azepin-2-yl)butyrate Yellowish viscous oil IR spectrum $\nu$ (liq) cm$^{-1}$: 1738 (COO) NMR spectrum $\delta$(CDCl$_3$) ppm: 1.25(3H,t,J=7 Hz), 1.60–3.50(13H,m),3.90–4.40(3H,m),4.85(1H,d,J=13 Hz),6.60–7.40(8H,m)

High resolution mass spectrum for $C_{23}H_{28}N_2O_2$ Calculated m/z: 364.2151 Found m/z: 364.2152

Example 38

Ethyl 5-(1,2,3,4,10,14b-Hexahydrodibenzo[c,f]pyrazino[1,2-a]azepin-2-yl)valerate Yellowish viscous oil IR spectrum $\nu$ (liq) cm$^{-1}$: 1736 (COO) NMR spectrum $\delta$(CDCl$_3$) ppm: 1.25(3H,t,J=7 Hz),1.40–3.50(15H,m),3.95–4.40(3H,m), 4.85(1H,d,J=13 Hz), 6.80–7.50(8H,m)

High resolution mass spectrum for $C_{24}H_{30}N_2O_2$ Calculated m/z: 378.2307 Found m/z: 378.2311

Example 39

Ethyl 6-(1,2,3,4,10,14b-Hexahydrodibenzo[c,f]Pyrazino[1,2-a]azepin-2-yl)caproate Yellowish viscous oil IR spectrum $\nu$ (liq) cm$^{-1}$: 1738 (COO) NMR spectrum $\delta$(CDCl$_3$) ppm: 1.25(3H,t,J=7 Hz),1.30–3.50(17H,m), 3.95–4.40(3H,m),4.85(1H,d,J=13 Hz), 6.70–7.40(8H,m)

High resolution mass spectrum for $C_{25}H_{32}N_2O_2$ Calculated m/z: 392.2464 Found m/z: 392.2453

Example 40

2-(1,2,3,4,10,14b-Hexahydrodibenzo[c,f]pyrazino[1,2-a]azepin-2-yl)acetic acid

2N Aqueous sodium hydroxide solution (5 ml) was added to a solution of 1.68 g of ethyl 2-(1,2,3,4,10,14b-hexahydrodibenzo[c,f]pyrazino[1,2-a]azepin-2-yl)acetate in 17 ml of methanol. The solution was refluxed for 30 min and then concentrated. The residue was dissolved in hot water and the solution was neutralized with 0.5N hydrochloric acid. The precipitates were collected by filtration to give 1.33 g of colorless crystals, which were recrystallized from aqueous ethanol to give colorless needles, mp 162°–163° C.

Analysis for $C_{19}H_{20}N_2O_2 \cdot 2H_2O$ Calculated C,66.26; H,7.02; N,8.13 Found C,66.45; H,6.88; N,8.12

The compounds of Example 41 to 44 were prepared in the same manner as described in Example 40.

Example 41

3-(1,2,3,4,10,14b-Hexahydrodibenzo[c,f]pyrazino[1,2-a]azepin-2-yl)propionic acid Colorless crystals, mp 195°–197° C. (H$_2$O-EtOH)

Analysis for $C_{20}H_{22}N_2O_2 \cdot \frac{1}{2}H_2O$ Calculated C,72.48; H,6.99; N,8.45 Found C,72.34; H,6.81; N,8.45

Example 42

4-(1,2,3,4,10,14b-Hexahydrodibenzo[c,f]pyrazino[1,2-a]azepin-2-yl)butyric acid

Colorless crystals, mp 104°–105° C. (H$_2$O-EtOH)

Analysis for C$_{21}$H$_{24}$N$_2$O$_2$ Calculated C,74.97; H,7.19; N,8.33 Found C,74.95; H,7.13; N,8.35

Example 43

5-(1,2,3,4,10,14b-Hexahydrodibenzo[c,f]pyrazino[1,2-a]azepin-2-yl)valeric acid

Colorless prisms, mp 218°–219° C. (H$_2$O-EtOH)

Analysis for C$_{22}$H$_{26}$N$_2$O$_2$ Calculated C,75.40; H,7.48; N,7.99 Found C,75.56; H,7.56; N,7.96

Example 44

6-(1,2,3,4,10,14b-Hexahydrodibenzo[c,f]pyrazino[1,2-a]azepin-2-yl)caproic acid

Colorless crystals, mp 181°–182° C. (H$_2$O-EtOH)

Analysis for C$_{23}$H$_{28}$N$_2$O$_2$ Calculated C,75.79; H,7.74; N,7.69 Found C,75.95; H,7.79; N,7.58

Example 45

Tablets of a pharmaceutical preparation according to the present invention are prepared in the usual manner using the following constituents:

| Compound of the present invention | 10 mg |
|---|---|
| Lactose | q.s. |
| Corn starch | 34 mg |
| Magnesium stearate | 2 mg |
| Hydroxypropylmethylcellulose | 8 mg |
| Polyethyleneglycol 6000 | 0.5 mg |
| Titanium oxide | 0.5 mg |

Example 46

Capsules of a pharmaceutical preparation according to the present invention are prepared in the usual manner using the following constituents:

| Compound of the present invention | 10 mg |
|---|---|
| Lactose | q.s |
| Calcium carboxymethylcellulose | 15 mg |
| Hydroxypropylcellulose | 2 mg |
| Magnesium stearate | 2 mg |
| | 100 mg |

Example 47

Powders of a pharmaceutical preparation according to the present invention are prepared in the usual manner using the following constituents:

| Compound of the present invention | 20 mg |
|---|---|
| Lactose | q.s. |
| D-Mannitol | 500 mg |
| Hydroxypropylcellulose | 5 mg |
| Talc | 2 mg |
| | 1000 mg |

Example 48

Injections of a pharmaceutical preparation according to the present invention are prepared in the usual manner using the following constituents:

| Compound of the present invention | 1 mg |
|---|---|
| Glucose | 50 mg |
| Hydrochloric acid | q.s. |
| Distilled water for injection | q.s. |
| | 2 ml |

Example 49

Suppositories of a pharmaceutical preparation according to the present invention are prepared in the usual manner using the following constituents:

| Compound of the present invention | 5 mg |
|---|---|
| Hard fat | 1295 mg |
| | 1300 mg |

Example 50

Plasters of a pharmaceutical preparation according to the present invention are prepared in the usual manner using the following constituents:

| Compound of the present invention | 10 mg |
|---|---|
| Gelatin | 1100 mg |
| Polyvinylalcohol | 250 mg |
| Methylcellulose | 100 mg |
| Glycerin | 1500 mg |
| Kaolin | 850 mg |
| Sodium polyacrylate | 50 mg |
| Polybutene | 150 mg |
| Purified water | 990 mg |
| | 5000 mg |

What is claimed is:

1. A polycyclic compound represented by the following formula:

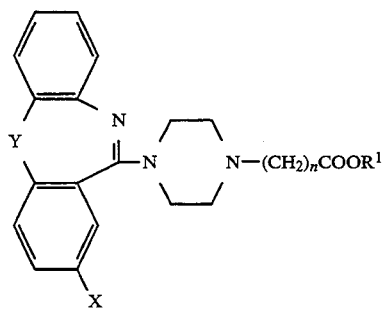

wherein R$^1$ represents a hydrogen atom; n represents an integer of from 1 to 5; X represents a hydrogen atom or a halogen atom; and Y represents an oxygen atom or a sulfur atom;

or a pharmacologically acceptable salt thereof.

2. A polycyclic compound represented by the following formula:

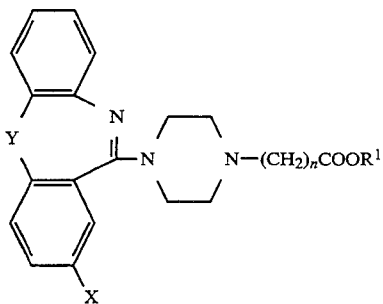

wherein R¹ represents a hydrogen atom; n represents an integer of from 1 to 5; X represents a hydrogen atom or a halogen atom; and Y represents a methylene group;

or a pharmacologically acceptable salt thereof.

3. A pharmaceutical composition comprising an effective amount of a polycyclic compound represented by the following formula:

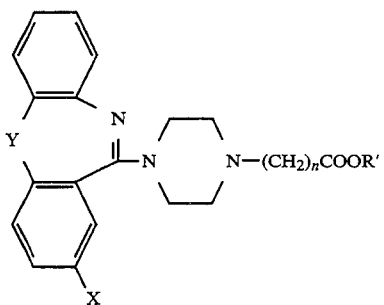

wherein R¹ represents a hydrogen atom; n represents an integer of from 1 to 5; X represents a hydrogen atom or a halogen atom; and Y represents an oxygen atom or a sulfur atom;

or a pharmacologically acceptable salt thereof, together with a pharmaceutically acceptable carrier or coating.

4. A pharmaceutical composition comprising an effective amount of a polycyclic compound represented by the following formula:

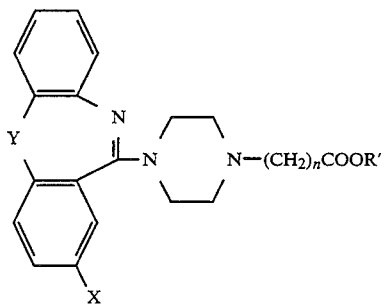

wherein R¹ represents a hydrogen atom; n represents an integer of from 1 to 5; X represents a hydrogen atom or a halogen atom; and Y represents a methylene group;

or a pharmaceutically acceptable salt thereof, together with a pharmaceutically acceptable carrier or coating.

5. 4-(2-Chlorodibenz[b,f][1,4]oxazepin-11-yl)-1-piperazinepropionic acid and a pharmacologically acceptable salt thereof.

6. 4-(2-Chlorodibenzo[b,f][1,4]oxazepin-11yl)-1-piperazinebutyric acid and a pharmacologically acceptable salt thereof.

7. 4-(2-Chlorodibenzo[b,f][1,4]thiazepin-11-yl)-1-piperazinepropionic acid and a pharmacologically acceptable salt thereof.

8. 4-(2-Chlorodibenzo[b,f][1,4]thiazepin-11-yl)-1-piperazinebutyric acid and a pharmacologically acceptable salt thereof.

9. 4-(11H-Dibenz[b,e]azepin-6yl)-1-piperazinepropionic acid and a pharmacologically acceptable salt thereof.

10. 4-(11H-dibenz[b,e]azepin-6-yl)-1-piperazinebutyric acid and a pharmacologically acceptable salt thereof.

* * * * *

UNITED STATES PATENT AND TRADEMARK OFFICE
CERTIFICATE OF CORRECTION

PATENT NO. : 5,344,828
DATED : September 6, 1994
INVENTOR(S) : Sawanishi et al.

Page 1 of 2

It is certified that error appears in the above-indentified patent and that said Letters Patent is hereby corrected as shown below:

Column 4, line 31, before "a iodine" insert --or--;

Column 8, line 22, change "$O_3$" to --$O_2$--;

Column 9, line 24, change "5hy-" to --5-hy---;

Column 10, line 5, change "3.4 g" to --3.14 g--;

Column 10, line 36, change "[1,49" to --[1,4]--;

Column 11, line 5, delete "Example 9";

Column 11, between lines 5 and 6, insert the heading --Example 9--;

Column 11, lines 12-13, delete "Example 10";

Column 11, between lines 12 and 13, insert the heading --Example 10--;

Column 11, line 21, change "[1,49" to --[1,4]--;

Column 12, line 41, change "1piperazinecaproate" to --1-piperazinecaproate--;

Column 13, line 37, change "($H_2$-EtOH)" to --($H_2O$-EtOH)--;

Column 13, line 44, delete the hyphen [-] at the end of the line;

Column 13, line 61, delete the hyphen [-] at the end of the line;

Column 14, line 2, change "[t" to --H--;

Column 14, line 7, delete the hyphen [-] at the end of the line;

Column 14, line 47, change "Piperazineacetic" to --piperazineacetic--;

Column 14, line 49, delete the hyphen [-] at the end of the line;

Column 15, line 24, delete the hyphen [-] at the end of the line;

Column 15, line 44, delete the hyphen [-] at the end of the line;

Column 15, line 59, delete the hyphen [-] at the end of the line;

UNITED STATES PATENT AND TRADEMARK OFFICE
CERTIFICATE OF CORRECTION

PATENT NO. : 5,344,828

DATED : September 6, 1994

INVENTOR(S) : Sawanishi et al.

It is certified that error appears in the above-indentified patent and that said Letters Patent is hereby corrected as shown below:

Column 16, line 3, delete "NMR spec-";

Column 16, line 4, delete "trum" and insert --NMR spectrum--;

Column 16, line 13, delete the hyphen [-] at the end of the line;

Column 16, line 24, delete the hyphen [-] at the end of the line;

Column 16, line 35, delete the hyphen [-] at the end of the line;

Column 16, line 36, change "Pyrazino" to --pyrazino--;

Column 17, line 34, insert underlining under "0.5 mg";

Column 17, before line 35, insert under "0.5 mg" the following -- 120 mg --;

IN THE CLAIMS:

Claim 3, Column 19, in the formula, change "COOR'" to --COOR$^1$--;

Claim 4, Column 20, in the formula, change "COOR'" to --COOR$^1$--;

Claim 9, Column 20, line 39, change "6yl)" to --6-yl)--.

Signed and Sealed this

Thirty-first Day of January, 1995

Attest:

BRUCE LEHMAN

Attesting Officer

Commissioner of Patents and Trademarks